United States Patent [19]
Thakore

[11] Patent Number: 5,135,716
[45] Date of Patent: Aug. 4, 1992

[54] DIRECT MEASUREMENT OF HDL CHOLESTEROL VIA DRY CHEMISTRY STRIPS

[75] Inventor: Yatin B. Thakore, East Brunswick Township, Middlesex County, N.J.

[73] Assignee: Kingston Diagnostics, L.P., Dayton, N.J.

[21] Appl. No.: 660,429

[22] Filed: Feb. 25, 1991

Related U.S. Application Data
[63] Continuation-in-part of Ser. No. 379,009, Jul. 12, 1989.

[51] Int. Cl.⁵ .......................................... G01N 21/77
[52] U.S. Cl. .......................................... 422/56; 422/58; 422/73; 435/11; 435/805; 436/17; 436/71
[58] Field of Search .................. 422/56, 57, 58, 73; 436/17, 71; 435/11, 805

[56] References Cited

U.S. PATENT DOCUMENTS

| | | | |
|---|---|---|---|
| 3,992,158 | 11/1976 | Przybylowicz et al. | 422/56 |
| 4,188,188 | 2/1980 | Willner et al. | 435/11 X |
| 4,210,557 | 7/1980 | Handschuh | 436/17 |
| 4,226,713 | 10/1980 | Goldberg | 435/11 X |
| 4,366,244 | 12/1982 | Pascal | 435/11 |
| 4,786,603 | 11/1988 | Wielinger et al. | 436/69 |
| 4,816,224 | 3/1989 | Vogel et al. | 435/170 |
| 4,820,489 | 4/1989 | Rothe et al. | 422/56 |
| 4,839,297 | 6/1989 | Frietag et al. | 436/170 |
| 4,851,335 | 7/1989 | Kerscher et al. | 435/11 |
| 4,857,453 | 8/1989 | Ullman et al. | 435/7 |
| 4,861,712 | 8/1989 | Bartl et al. | 435/13 |
| 4,876,067 | 10/1989 | Deneke | 422/56 |
| 4,892,815 | 1/1990 | Kerscher et al. | 435/7 |
| 4,906,439 | 3/1990 | Grenner | 422/56 |
| 4,943,522 | 7/1990 | Eisinger et al. | 435/7 |
| 4,987,085 | 1/1991 | Allen et al. | 422/56 X |
| 5,034,332 | 7/1991 | Rapacz et al. | 435/11 X |

*Primary Examiner*—James C. Housel
*Assistant Examiner*—Jeffrey R. Snay
*Attorney, Agent, or Firm*—Kenneth P. Glynn

[57] ABSTRACT

A device for determining HDL cholesterol by obtaining plasma from whole blood and determining the HDL cholesterol level from the plasma. The device includes an inert substrate support or an active substrate support (e.g. one or the other layers), a physical transport medium, a microporous plasma separation membrane connected to the physical transport medium, at least one plasma collecting test membrane, a filtering membrane, LDL and VLDL reactants to form LDL and VLDL precipitates and an optional carrier precipitation membrane. The plasma collecting test membrane has reactants which will react with HDL cholesterol and indicate the HDL cholesterol level quantitatively. The filtering membrane may be located between the microporous plasma separation membrane and the transport medium or between the microporous plasma membrane and the plasma collecting test membrane and its function is to block the precipitated particles from reaching the test zone. The LDL and VLDL reactants which form precipitates of LDL and VLDL may be located anywhere upstream from the plasma collecting test membrane, i.e., within one or more of the transport medium, the microporous plasma separation membrane, the filtering membrane and the optional carrier separation membrane.

91 Claims, 8 Drawing Sheets

DIRECT MEASUREMENT OF HDL CHOLESTEROL VIA DRY CHEMISTRY STRIPS

REFERENCE TO A RELATED APPLICATION AND INCORPORATION BY REFERENCE

This application is a continuation-in-part of pending U.S. patent application Ser. No. 07/379,009, entitled "Device and Method for Separation of Plasma from Blood and Determination of Blood Analytes" filed on Jul. 12, 1989 by Yatin B. Thakore and Karen L. Swanson. The drawings thereof are incorporated herein by reference in their entirety.

BACKGROUND OF THE INVENTION

1. Field of the Invention

The present invention is directed to a device for determining high density cholesterol (HDL) which allows the user to obtain rapid, reliable results in a simple manner. More specifically, the present invention is directed to HDL test strips utilizing dry chemistry.

2. Prior Art

Measurement of high density cholesterol, particularly in conjunction with cholesterol measurement, has been proven to be an effective indicator of potential risk to atherosclerotic cardiovascular disease (CVD). Therefore, the determination of high density lipoprotein (HDL) cholesterol has become important and common in clinical laboratories.

The traditional method of measuring these analytes is via wet chemistry, although commercial dry chemistry tests are available for total cholesterol. HDL cholesterol measurements, however, continue to be time consuming.

For a measurement of high density cholesterol, one needs to separate serum/plasma from whole blood by traditional methods of clotting or centrifugation. The separated plasma or serum is then added in a precise ratio with a precipitant system and mixed thoroughly. The plasma/precipitant mixture is allowed to sit for 5-25 minutes to allow the completion of precipitate formation and agglomeration of the precipitated particles. After this step, the mixture is centrifuged to allow the precipitate to form a cake at the bottom of the centrifuge tube and the supernatant containing high density lipoprotein (HDL) is carefully withdrawn. The cholesterol associated with this HDL fraction (HDL cholesterol) is then measured either via wet chemistry or could be measured by a cholesterol dry strip if designed to do so.

Another common method used for HDL cholesterol measurement is ultracentrifugation wherein various cholesterol-containing fractions are separated in an ultracentrifuge. This method is even more laborious and time consuming and requires considerable technical skill. Only a few reference laboratories are equipped to measure HDL cholesterol in this way and this method is quite expensive. Electrophoresis of lipoproteins has also been used but this again is slow, expensive and semi-quantitative. It is usually used only as an adjunct to other quantitative methods.

HDL cholesterol measurements therefore tend to be time consuming with manual methods. These steps can be automated, and for a large volume of sample throughput as in many clinical laboratories, analyzers which can dispense and process the reagents automatically are available but can be quite complex and expensive.

Many patents have been issued which describe the various physical arrangements for blood testing. These include systems which involve lateral or horizontal movement of the blood, as well as plasma testing. For example, U.S. Pat. No. 4,876,067 to Deneke et al; U.S. Pat. Nos. 4,861,712 to Bartl et al; 4,839,297 to Freitag et al and U.S. Pat. No. 4,786,603 to Wielinger et al, all assigned to Boehringer Mannheim GmbH, describe test carriers and methods for analytical determination of components of bodily fluids, including separating plasma from blood using glass fibers and the like. These patents, however, all teach systems which require some type of rotation of test pads or a portion of the test pads during use. U.S. Pat. No. 4,816,224 to Vogel et al also assigned to Boehringer Mannheim GmbH, describes a device for separating plasma or serum from whole blood and analyzing the serum using a glass fiber layer having specific dimensions and absorption to separate out the plasma from the whole blood for subsequent reaction.

U.S. Pat. No. 4,857,453 to Ullman et al describes a device for performing an assay using capillary action and a test strip containing sealed liquid reagents including visible indicators. U.S. Pat. No. 4,906,439 to Grenner describes a diagnostic device for efficiently and accurately analyzing a sample of bodily fluid using fluid delivery in a lateral movement via flow through channels or grooves.

In addition to the above patents which are representative of the prior art showing various physical types of systems for blood testing and the like, recent patents have issued which are directed to the particular chemistry for the determination of HDL cholesterol. Thus, U.S. Pat. Nos. 4,851,335 to Kerscher et al and U.S. Pat. No. 4,892,815 also to Kerscher et al, describe specific types of processes and reagents for HDL cholesterol determination. These inventions take advantage of the different reactivities of HDL cholesterol versus cholesterol contained in other low and very low density lipoproteins (LDL and VLDL). These inventions thereby eliminate the traditional separation steps necessary for HDL cholesterol determination. The measurements are kinetic, meaning the rate of reaction of HDL cholesterol is monitored after LDL and VLDL cholesterol have all been reacted and requires careful control of time and temperature. Precisely controlled volumes of reagents are added at precise times in a prescribed manner. Measurement times are 3-10 minutes (U.S. Pat. No. 4,892,815). Even though this presents a significant improvement, for accurate results, it needs careful operator supervision if done manually or expensive instrumentation if automated.

Notwithstanding all of the above prior art, there has been no simple combined physical system and chemistry which enables the user to simply, efficiently and quickly obtain HDL cholesterol readings.

The present invention describes another approach, wherein the sample processing, including plasma separation, precipitant metering, precipitate separation as well as HDL cholesterol reactions are built into a strip such that user manipulations are minimized and HDL cholesterol can be measured in one to two minutes directly from whole blood. The method measures the end-point of the reaction and therefore precise time and temperature controls are not necessary. This method uses a device similar to that described in the parent application (of which this is a Continuation-in-Part, fully referenced and incorporated herein above) for separation of plasma and for measurement of cholesterol, except that specific dry chemistry for HDL determination is used. The device employs a tangential flow of blood across the blood cell separation membrane. HDL dry chemistry precipitation reagents as well as precipitate filters are built into the present invention device.

SUMMARY OF THE INVENTION

The present invention involves a device for determining HDL cholesterol by obtaining plasma from whole blood and determining the HDL cholesterol esterol level from the plasma. The device includes an inert substrate support or an active substrate support (e.g. one or the other layers), a physical transport medium, a microporous plasma separation membrane connected to the physical transport medium, at least one plasma collecting test membrane, a filtering membrane, LDL and VLDL reactants to form LDL and VLDL precipitates and an optional carrier precipitation membrane. The plasma collecting test membrane has reactants which will react with HDL cholesterol and indicate the HDL cholesterol level quantitatively. The filtering membrane may be located between the microporous plasma separation membrane and the transport medium or between the microporous plasma membrane and the plasma collecting test membrane and its function is to block the precipitated particles from reaching the test zone. The LDL and VLDL reactants which form precipitates of LDL and VLDL may be located anywhere upstream from the plasma collecting test membrane, i.e., within one or more of the transport medium, the microporous plasma separation membrane, the filtering memberance and the optional carrier separation membrane.

BRIEF DESCRIPTION OF THE DRAWINGS

The present invention described in the specification herein will be more fully understood when taken in conjuction with the drawings appended hereto, which show as follows.

DETAILED DESCRIPTION OF THE INVENTION

Figure 1:
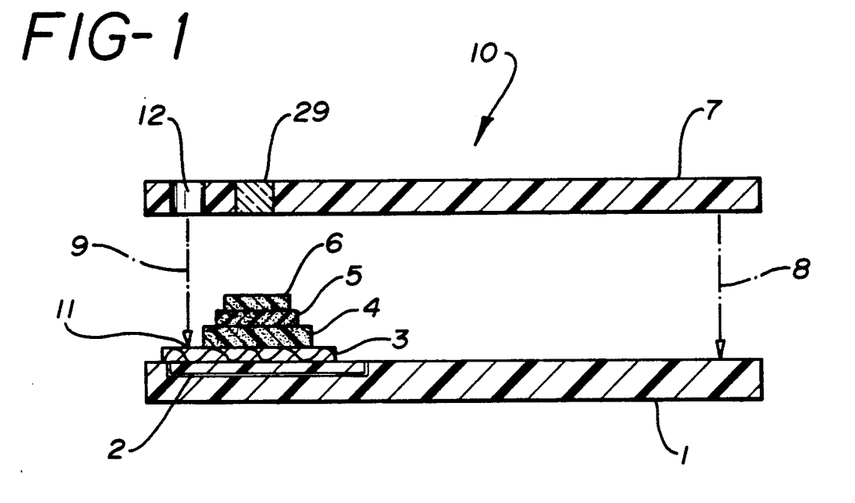
FIG. 1 shows a side cut view of a present invention device which precipitates certain lipoproteins in the separation membrane.

FIG. 1 represents one embodiment of the present invention. The device 10 has an inert substrate 1. In this case, LDL and VLDL precipitating reactants are added to the microporous plasma separation membrane 4 and plasma collecting test membrane 6 contains the dry chemistry HDL cholesterol reagents of the type described above. During use, blood is added to the blood application area 11 of physical transport medium 3. It travels along the channels 2 and physical transport medium 3, in this case, a transport membrane sheet which is a woven mesh of monofilament polyester with 17 micron mesh opening (Tetko, Briarcliff, N.Y.) and having a thickness of about 75 microns. Woven fabric, non-woven fabric, gauze and monofilament yarn are among the many choices for the transport membrane sheet shown as physical transport medium 3. Plasma separation as well as precipitation is handled by a microporous plasma separation membrane 4, in this case, 5 micron nitrocellulose (Schleicher and Schuell, Keene, N.H.). A filtering membrane 5 filters off the LDL and VLDL precipitates and prevents them from reaching the plasma collecting test membrane 6. Filtering membrane 5 was a 0.4 micron hydrophilic polycarbonate membrane (Poretics Corp., Livermore, C.A.) used without treatment or 0.2 micron nylon (Micron Separations, Inc., Westboro, M.A.) or 0.8 micron polysulfone (Gelman Sciences, Ann Arbor, M.I.). The latter two were saturated with 5% or 10% aqueous solution of polyethylene glycol (molecular weight 1000 daltons) and dried. Polyethylene glycol (PEG) was used as a wetting agent. In this embodiment, plasma collecting test membrane 6, as mentioned, contains enzymes and chromogens for cholesterol assay so that plasma reaching it (now devoid of LDL and VLDL components) reacts with the reagents in plasma collecting test membrane 6, producing a colored reaction, the intensity of color being proportional to HDL cholesterol concentration. In this case, plasma collecting test membrane 6 was a 0.45 micron nylon membrane (Micron Separations, Inc, Westboro, M.A.). Top sheet 7 with orifice 12 and transparent area 29 is adhered over the tops of the other components as shown by arrows 8 and 9. Transparent area 29 is comprised of an aperture covered with a transparent, oxygen permeable membrane to ensure oxygen transport to the oxygen-utilizing reaction taking place in plasma collecting test membrane 6. A drop of blood may be applied to the blood application area 11 of physical transport medium 3 through orifice 12 and the colorimetric reaction may be viewed through transparent area 29. Alternatively, one or more of the layers may be strong enough to support the device in the absence of an inert substrate support.

Figure 2:
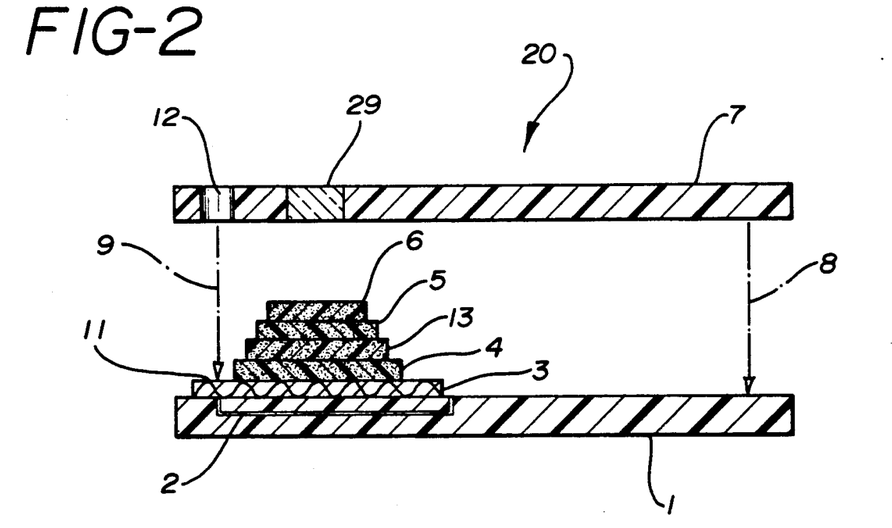
FIG. 2 shows a side cut view of a present invention device which precipitates certain lipoproteins in an extra carrier precipitant membrane.

FIG. 2 shows present invention device 20 wherein like parts to those shown in FIG. 1 are like numbered. In the embodiment of FIG. 1, LDL and VLDL precipitation is carried out from the whole blood itself, whereas the embodiment shown in FIG. 2 alternatively has an additional carrier precipitant membrane 13 added, containing the precipitant system so that precipitation is carried out after the plasma separation step on the plasma alone rather than on whole blood.

Figure 3:
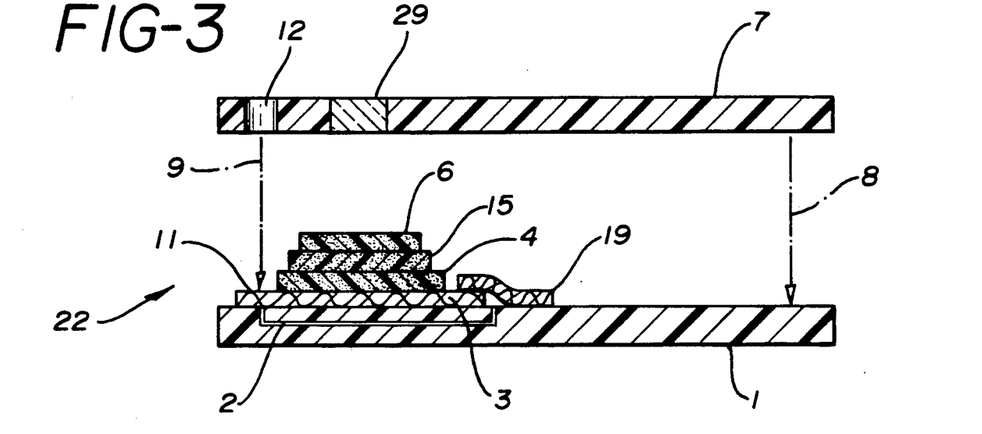
FIG. 3 shows a side cut view of a present invention device which includes an asymmetric membrane for the dual function of precipitation and filtering above and downstream of the microporous plasma separation membrane.

It is possible to place the precipitant elsewhere in the system, e.g. in the physical transport medium 3 or alternatively in grooves or channels 2 of the inert substrate 1 for precipitation from whole blood. In another alternative for precipitation from plasma, filtering membrane 5 could serve as the precipitant membrane, thereby eliminating carrier precipitant membrane 13, provided the filtering membrane pore size is appropriately chosen. This is shown in device 22 of FIG. 3 wherein like parts to FIG. 2 are like numbered. An asymmetric carrier separation membrane 15 placed atop microporous plasma separation membrane 4 serves dual roles of precipitation and filtration thereby replacing filtering membrane 5 and carrier precipitant membrane 13. Also included in FIG. 3 is absorbent storage medium 19 which absorbs excess applied blood sample to prevent excess blood from retarding the effectiveness of plasma collecting test membrane 6.

Some of these variations in the basic configurations shown in FIGS. 1 and 2 will become clear, once the requirements and functions of various components are described in more detail in the paragraphs that follow.

The functions of the microporous plasma separation membrane 4 and components 1,2 and 3 are described in detail in copending parent U.S. patent application Ser. No. 07/379,009 referenced above. Essentially, tangential flow of blood on the underside of microporous plasma separation membrane 4 is facilitated by components 2 and 3. The capillary pull draws the blood on the underside and through the cross-section of membrane 4 which retains the red cells while delivering clean plasma on the top surface which can be drawn into the subsequent filtering membrane 5 and/or carrier precipitant membrane 13.

Whether precipitation is carried out on whole blood or plasma, the precipitant systems are adapted from conventional liquid chemistry. In liquid chemistry, which uses plasma or serum, four principal precipitation systems are used:

(1) Dextran sulfate (DS) (50,000 or 500,000 dalton molecular weight) generally with magnesium chloride ($MgCl_2$) as the source for divalent cations;
(2) Heparin-manganese chloride;
(3) Polyethylene glycol (PEG) (6000 dalton molecular weight);
(4) Phosphotungstic acid-sodium salt, usually in conjunction with $MgCl_2$.

In general, all the systems correlate quite well with each other as well as with the reference method of ultracentrifugation. All four are being used extensively and several commercial kits are available for wet chemistry assays of HDL cholesterol using these reagents.

Any of these system could be adapted for dry chemistry strips; however, for precipitation from blood, the first three are preferable since they do not hemolyze the blood.

The choice of membrane or substrate for loading these precipitants is not particularly critical. In the case of polyethylene glycol of 6000 dalton molecular weight, however, a more open matrix is necessary (pore size of at least 10 microns and preferably in the 20–100 micron range). Otherwise PEG-6000, being waxy, clogs the pores and prevents HDL from reaching the plasma collecting test membrane 6 or effectively overprecipitates the HDL fraction. When using the system embodied in FIG. 1, the choice of microporous plasma separation membrane 4 will dictate the matrix for the precipitant, with a 3-8 micron pore size membrane being a preferred choice. A 5 micron pore-size membrane of nitrocellulose works quite well although cellulose is also one of many acceptable choices.

When the precipitation is carried out on plasma recovered on-line from whole blood as in FIG. 2, carrier precipitant membrane 13 may be an open matrix or a microfilter and the pore size is not particularly critical since filtering membrane 5 is used downstream between this membrane and the plasma collecting test membrane 6. The main requirements of this membrane are hydrophilicity, (i.e. its ability to absorb plasma readily from microporous plasma separation membrane 4) and the ability to release the plasma to the filtering membrane 5. From this perspective it is better to avoid membrane which are too fine in pore size (<0.1 micron) because they may hold the plasma too tightly due to very high capillary forces and the filtering membrane 5 downstream may not be able to pull in the plasma containing the precipitate.

Figure 4:
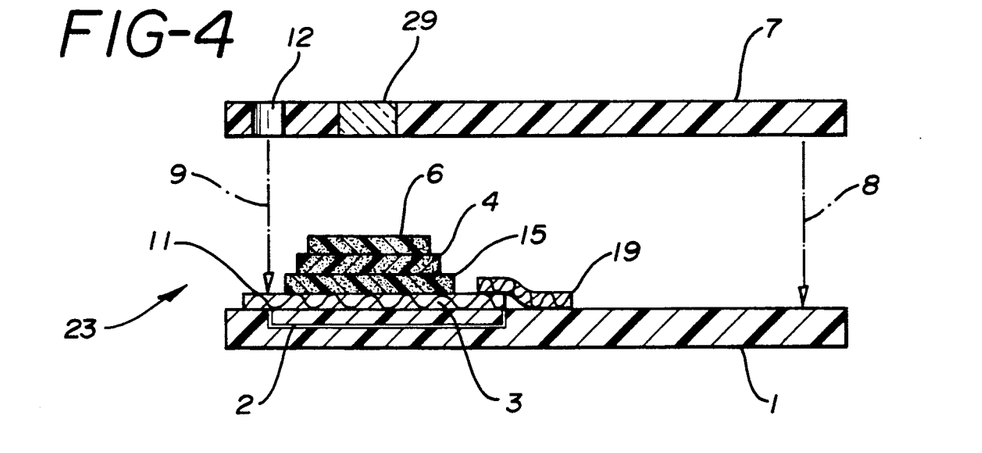
FIG. 4 shows a side cut view of a present invention device which includes an asymmetric membrane for the dual function of precipitating and filtering below and upstream of the microporous plasma separation membrane.

FIG. 4 shows present invention device 23 wherein like parts to those shown in FIG. 3 are like numbered. Asymmetric carrier separation membrane 15 acts both as a precipitant membrane and filtering membrane and, in this embodiment, is located below and upstream from microporous plasma separation membrane 4 so that precipitation and filtering is taking place on whole blood. The precipitant reactants could also be in physical transport medium 3 or anywhere upstream of microporous plasma separating membrane 4. Whether located upstream or downstream of carrier separation membrane 4, the smallest pore sizes of asymmetric carrier separation membrane 15 should be less than 1 micron and preferably less than 0.45 microns to assure that no precipitate reaches the plasma collecting test membrane 6. It is especially desirable to use a membrane which is asymmetric, i.e. its pores are tapered so that its larger pores are below and upstream of its smaller pores. One could also use a composite membrane with similar characteristics. Yet another approach for filtering membrane 5 is to use a membrane with ultramicroporous structure with pore size in the range of 0.01 to 0.1 microns. This can combine the functions of both filtering membrane 5 and carrier precipitant membrane 13 in a different manner. HDL particles are very small in size 0.004–0.014 microns) whereas LDL particles are larger (0.018–0.03 microns) and VLDL even larger (<0.03 microns). Such a membrane then would be able to physically filter out larger LDL and VLDL particles without any need for precipitation or with only limited help from precipitants. The smaller HDL particles would still be allowed to reach plasma collecting test membrane 6 for subsequent assay.

The concentrations of the precipitant can be adapted from those of liquid chemistries. However, in addition to the precipitants, it is advantageous to use hydrophilic non-volatile liquid or low molecular weigh additives such as low molecular weight polyethylene glycol (e.g. PEG of molecular weight 200–2000 daltons or other similar polyhydroxyl compounds.) Through it is not absolutely essential to use these compounds, it is preferable to do so, since upon loading the membrane with the precipitants and drying, the precipitants may bind to the membrane matrix and/or crystallize. The addition of PEG is especially useful in a two-component precipitant system consisting of polymers and co-ions (e.g. $DS-MgCl_2$ and $Heparin-MnCl_2$). In such cases the salts and the polymers may adsorb differently to the membrane matrix. As a result, depending on the precipitant system and the membrane matrix, some trial and error approaches may be needed to determine the exact concentrations and the polymer:co-ion ratio if they are loaded in the absence of such hydrophilic components, since they may not be readily soluble in blood or plasma in a predictable manner. The non-volatile hydrophilic components (e.g. PEG) keep the precipitants from adsorbing and from crystallizing and permit the movement of the precipitants in a predictable, readily soluble form for consistent release into the plasma (or blood). An additional advantage of PEG is that it increases the "wettability" and serum uptake of a variety of membranes, particularly of cellulosic nylon and polysulfone types. PEG (e.g. of molecular weight of 400–2000 daltons) can be used in concentrations of 2–20% in water or buffer with 5–10% concentration being in the optimum range. The precipitants are dissolved in the aqueous PEG solution at a concentration comparable to those used in liquid chemistry. For precipitation from whole blood (FIGS. 1 and 4), the precipitant concentration would be roughly half of that used in a plasma precipitation method (FIGS. 2 and 3). Typically, the membrane is saturated with the aqueous solution of PEG with the dissolved precipitants and allowed to dry. Upon drying, the precipitant membrane is ready to use.

The pore-size of any filtering membrane is important since it keeps the precipitated particles of LDL and VLDL from getting swept into plasma collecting test membrane 6 and thereby giving falsely high values for HDL cholesterol due to contamination of the final HDL sample. From experiments with wet chemistry, it was determined that immediately upon mixing the precipitant solution and the serum ("serum" and "plasma" are used interchangeably herein) the precipitated LDL and VLDL particles are somewhere in the range of 0.45–1.2 microns in size. With all precipitant systems, a 0.45 micron pore size filter can remove all the precipitate, whereas a 1.2 micron pore size filter is adequate only for PEG systems. Given enough time, however, the precipitate agglomerates and may become quite large in size. Thus, a very thick filtration membrane may function properly with larger pore sizes than indicated above.

In general, however, a microfilter with pore size of less than 1 micron is adequate to serve as a filtering membrane with 0.2–0.8 micron pore size being an optimum range. Other requirements such as wettability and an ability to transfer LDL and VLDL-free serum plasma to reagent membrane 6 downstream are similar to those described for carrier precipitant membrane 13 above. The wettability of filtering membrane 5 can also be enhanced if necessary by addition of wetting agents and/or surfactants such as low molecular weight PEG or derivatives of same.

As mentioned earlier, with an appropriately sized microporous membrane, filtering membrane 5 can be eliminated and the carrier precipitant membrane may perform dual roles of both a precipitant carrier membrane and filtering membrane.

Figure 5:
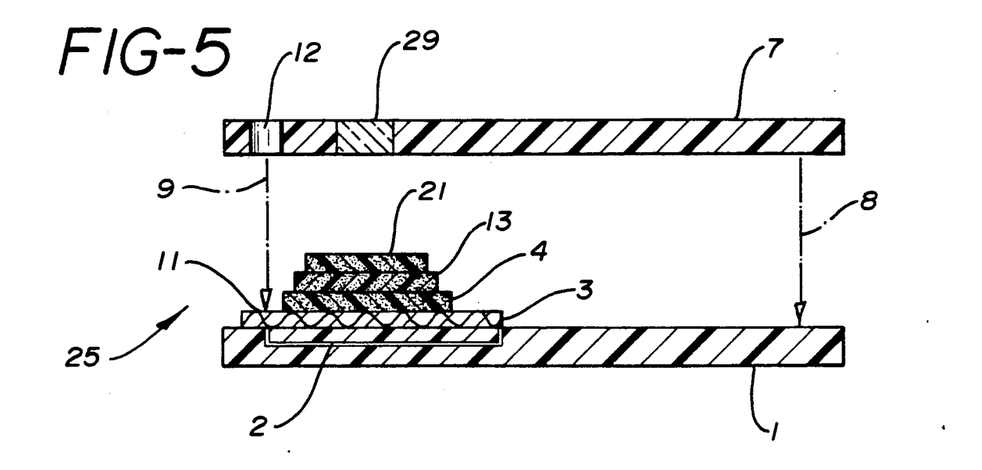
FIG. 5 shows a side cut view of a present invention device with an alternative arrangement using an asymmetric membrane for the dual purpose of filtering membrane and plasma collecting test membrane.

Conversely, one may choose to combine the functions of filtering and plasma receiving test membrane as shown in present invention device 25 of FIG. 5. In FIG. 5, like parts are like numbered to FIG. 2. FIG. 5 embodies an alternative arrangement in which a fine pore size (0.02–0.1 micron) filtering/plasma receiving test membrane 21 serves the dual roles of filtering membrane 5 and plasma collecting test membrane 6, thereby eliminating these two components from this embodiment. Again, it is preferable to use an asymmetric membrane with tapered pore structure, but with the "skin" side having finer pores facing the precipitant-containing carrier precipitant membrane 13 in FIG. 5. The precipitate is thereby prevented from coming in contact with the reagent system, which is confined to the opposite, more open section of the membrane.

The pore size of plasma collecting test membrane 6 is not particulary critical for the embodiments shown in FIGS. 1–4 as long as the membrane is sufficiently hydrophilic and is able to pull in HDL-containing plasma through its pore matrix. Additionally, the surface texture should be relatively smooth and uniform to obtain smooth colors from the color-forming reactions. If a chromogen system is loaded from an organic liquid such as acetone, alcohol or toluene, the membrane should be resistant to the appropriate solvent. Good wet strength is also desirable. Cellulosic and nylon membranes, particularly reinforced with a fabric within the membrane are especially good for this purpose and the pore size of 0.1–1 micron usually satisfies the requirements of surface smoothness and capillary pull. If the plasma collecting test membrane also serves as a filtering membrane as described earlier (FIG. 5), then an asymmetric membrane of 0.02–0.1 micron is a preferred choice.

The plasma collecting test membrane 6 (FIGS. 1 through 4) or filtering/plasma receiving test membrane 21 (FIG. 5) of the present invention device contains the enzymes cholesterol esterase, cholesterol oxidase and peroxidase along with buffer salts, activators, stabilizers and chromogen. The reagents are the same as those used in total cholesterol assays. The exact formulation is a matter of choice and also depends on the sources and purity of the enzymes. One typical formulation consists of cholesterol esterase (microbial @200 units/ml), cholesterol oxidase (Nocardia @40 units/ml), peroxidase (horseradish @200 units/ml) dissolved in 0.1M 2-[N-Morpholino] ethane sulfonic acid, potassium salt (MES) buffer at pH 6.7. The solution also contains 3% sodium cholate as activator. The reagent membrane is saturated with the enzyme solution, dried and then saturated in chromogen solution consisting of tetramethyl benzidine (TMB) and dioctysulfosuccinate, sodium salt (DOSS) at 5 mg/ml and 3 mg/ml respectively in acetone (or toluene) and allowed to dry.

In making a device to measure HDL, one has two primary choices as mentioned previously:
a) Precipitation of LDL and VLDL from whole blood either during or before cell separation as in the embodiments of FIGS. 1 and 4, respectively; or,
b) precipitation from plasma as in the embodiment of FIGS. 2,3 and 5.

When precipitation is from whole blood, the concentration of cells in the blood (hematocrit) may influence the values to some extent. In most liquid chemistry systems (with the possible exception of the PEG-6000 system), the ratio of plasma to precipitant is critical. Thus, a given concentration of precipitants will give a good correlation for patient HDL values in a certain defined hematocrit range since the precipitant and plasma ratios will vary somewhat with the hematocrit. However, when the precipitation is carried out on plasma as in FIGS. 2, 3 and 5 this ratio is maintained constant in the carrier precipitant membrane 13 and, as a result, the correlation between measured and actual HDL cholesterol values would be valid for the entire homatocrit range normally encountered.

The manner of use and the performance of the strips will become more clear in the examples that follow.

EXAMPLES

The examples given here illustrate the use of a dextan sulfate (500,000 daltons) and magnesium chloride ($MgCl_2.6H_2O$) precipitation system. The ratios between the two are identical to those used in liquid chemistries. For loading the precipitants, the reagents are dissolved at an appropriate concentration (specified in the examples) in 10% by volume of polyethylene glycol (molecular weight 400 daltons) or 10% by weight of PEG (1000 daltons) in deionized water. The precipitation membrane is then saturated with this solution and allowed to dry. In the examples channels are formed by having two raised plastic ridges (125 microns high, 1 mm wide and 15 mm long) 3 mm apart (center to center). Transport medium 3 was woven mesh of monofilament polyester with 17 micron mesh opening (Tetko. Briarcliff Manor, N.Y.). Microporous plasma separation membrane 4 was 5 micron nitrocellulose (Schleicher and Schuell, Keene, N.H.); filtering membrane 5 was 0.40 micron hydrophilic polycarbonate (Poretics Corp., Livermore, C.A.) used as is or 0.2 micron nylon (Micron Separation, Inc., Westboro, M.A.) or 0.8 micron polysulfone (Gelman Sciences, Ann Arbor, M.I.). The latter two were saturated with 5 or 10% aqueous solution of polyethylene glycol (molecular weight 1000 daltons) and dried. Polyethylene glycol was used as a wetting agent. Reagent-containing membrane 6 was 0.45 micron nylon membrane (Micron Separations, Inc.). When precipitation was carried out from the whole blood, the precipitation membrane was the same as the plasma separation membrane. When precipitation was carried out from plasma, carrier precipitant membrane 13 containing the precipitants was a 0.8 micron polysulfone membrane (Gelman Sciences). HDL concentration of Example patient samples was predetermined via conventional wet chemistry methods for purposes of comparison.

EXAMPLE 1

Figure 6:
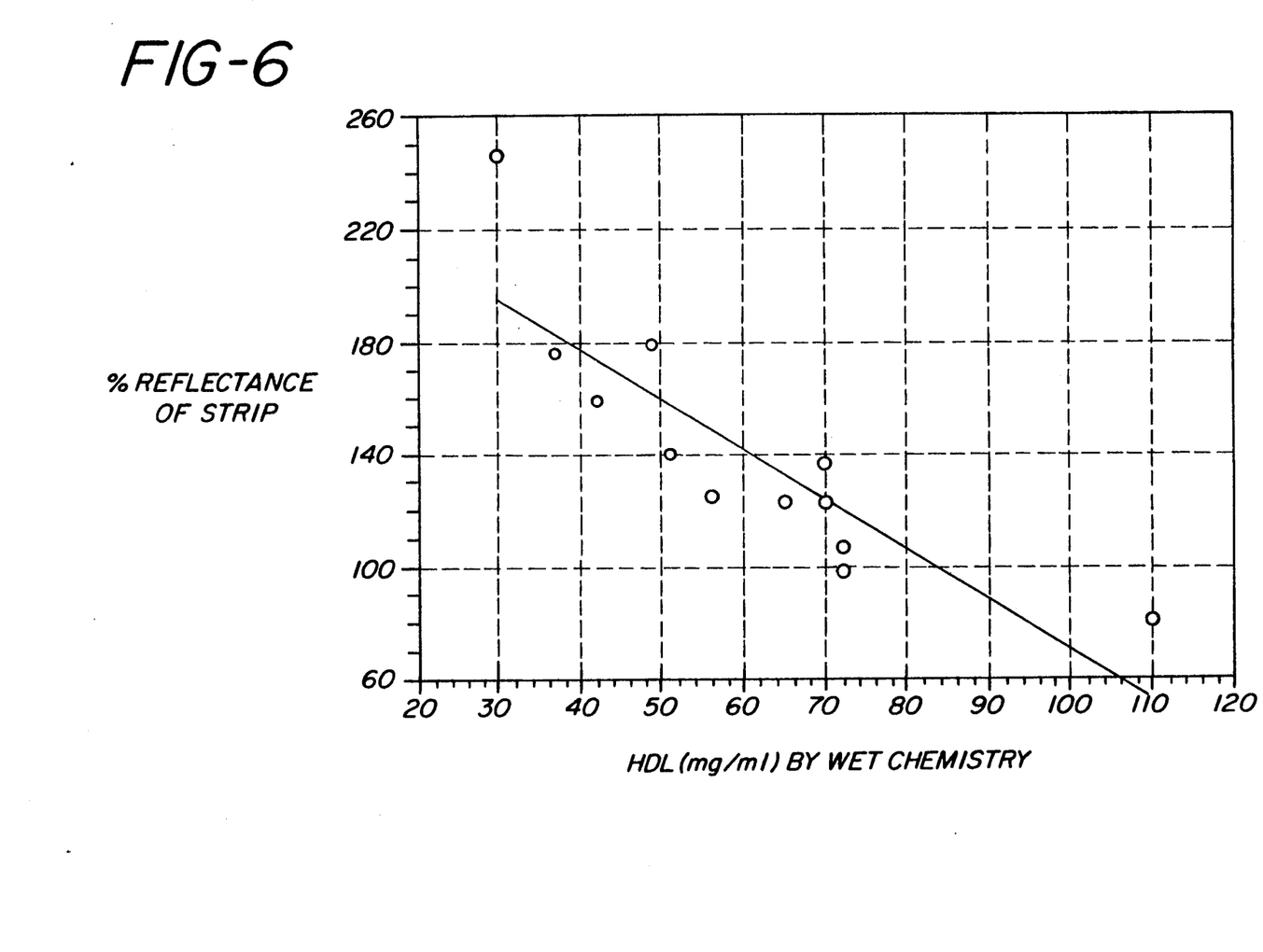
FIGS. 6 through 11 show various graphs of reflectance versus HDL level based on various types of test pads.

Devices of the embodiment shown in FIG. 1 were prepared for precipitants loaded in the plasma separation membrane 4. The concentrations of DS and $MgCl_2.6H_2O$ in the precipitant solution were 75 mg and 1522 mg/100 ml, respectively. Filtering membrane 5 was a 0.2 micron nylon filter. Twenty five microliters of patient plasma samples were applied and strips were pressed down until plasma collecting test membrane 6 was completely saturated. The color reaction was monitored in a reflectance meter until completion (usually under 2 minutes). The response of % reflectance vs. HDL concentration is shown in FIG. 6 which shows that the intensity of color is proportional to HDL concentration. The correlation coefficient calculated by linear regression was 0.86.

EXAMPLE 2

Figure 7:
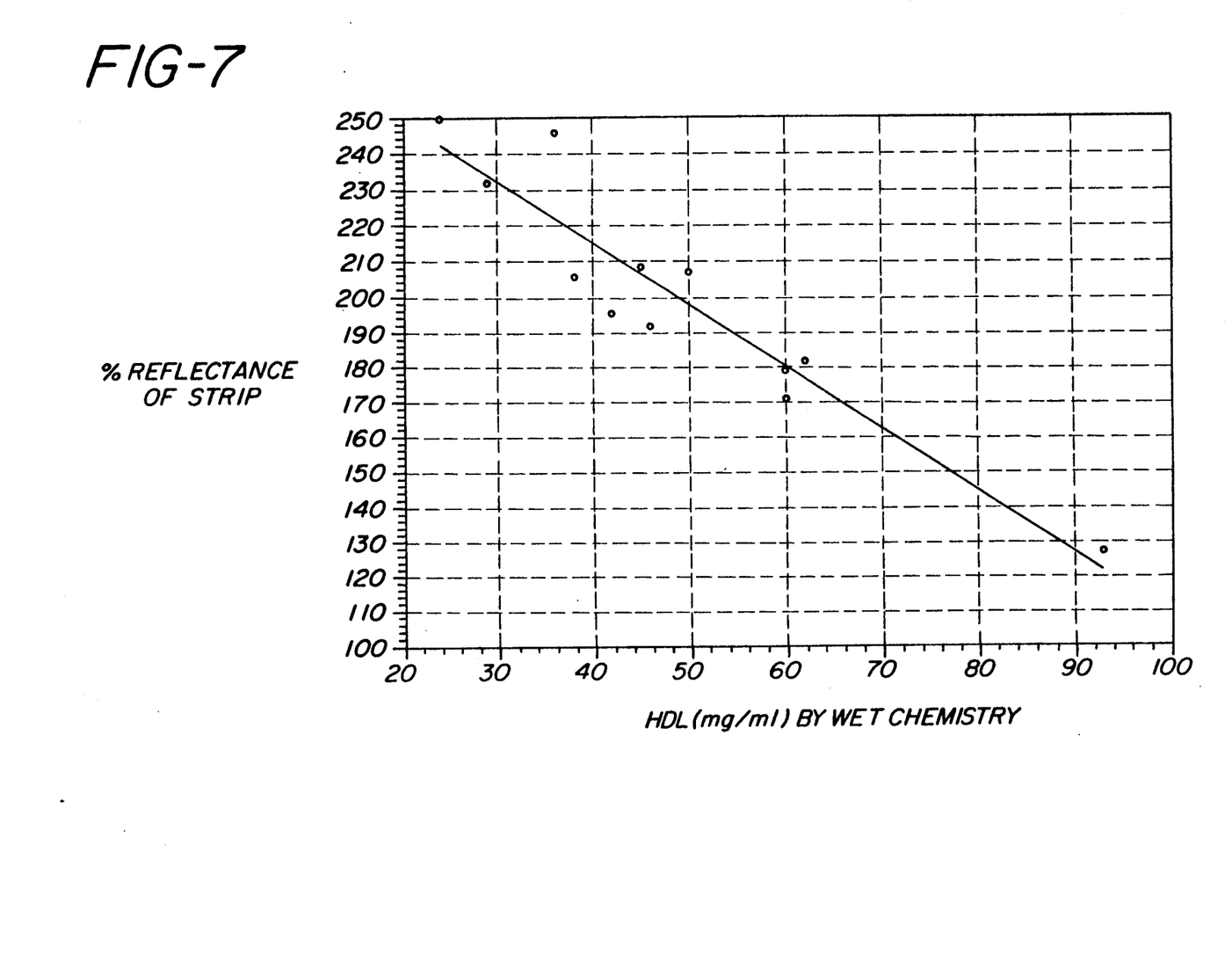

Similar devices and procedures as for Example 1 were used except that the concentrations of DS and $MgCl_2.6H_2O$ were 50 and 1015 mg/100 ml respectively and 40 microliter whole blood samples rather than plasma were applied. These devices in this example showed good color intensity versus HDL concentration correlations for patients with hematocrits <42%. The correlation coefficient determined by liner regression for a set of data on such samples in FIG. 7 is 0.94.

EXAMPLE 3

Figure 8:
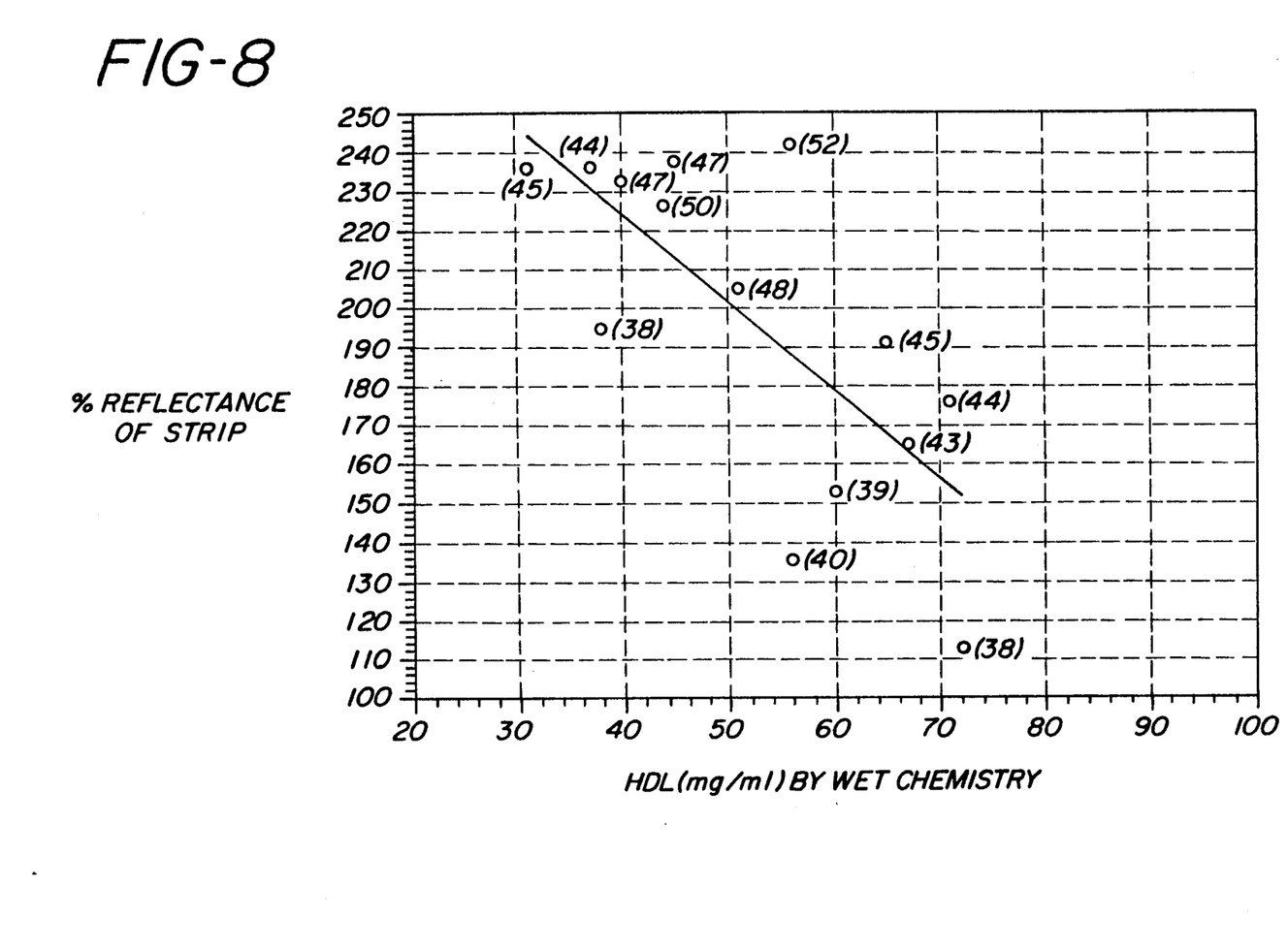

Devices and procedures similar to those in example 2 were used but the concentrations of precipitants DS and $MgCl_2.6H_2O$ were reduced to 35 and 710 mg/100 ml respectively. % Reflectance vs. HDL concentrations are shown in FIG. 8 for a sample population of 14 persons. The values in parentheses are hematocrit values. Whereas the lower hematocrit samples (<42%) are underprecipitated (darker colors or lower Reflectance than predicted by curve), the correlation for higher hematocrit samples (43–50%) is quite good (correlation coefficient 0.94 by linear regression analysis).

EXAMPLE 4

Figure 9:
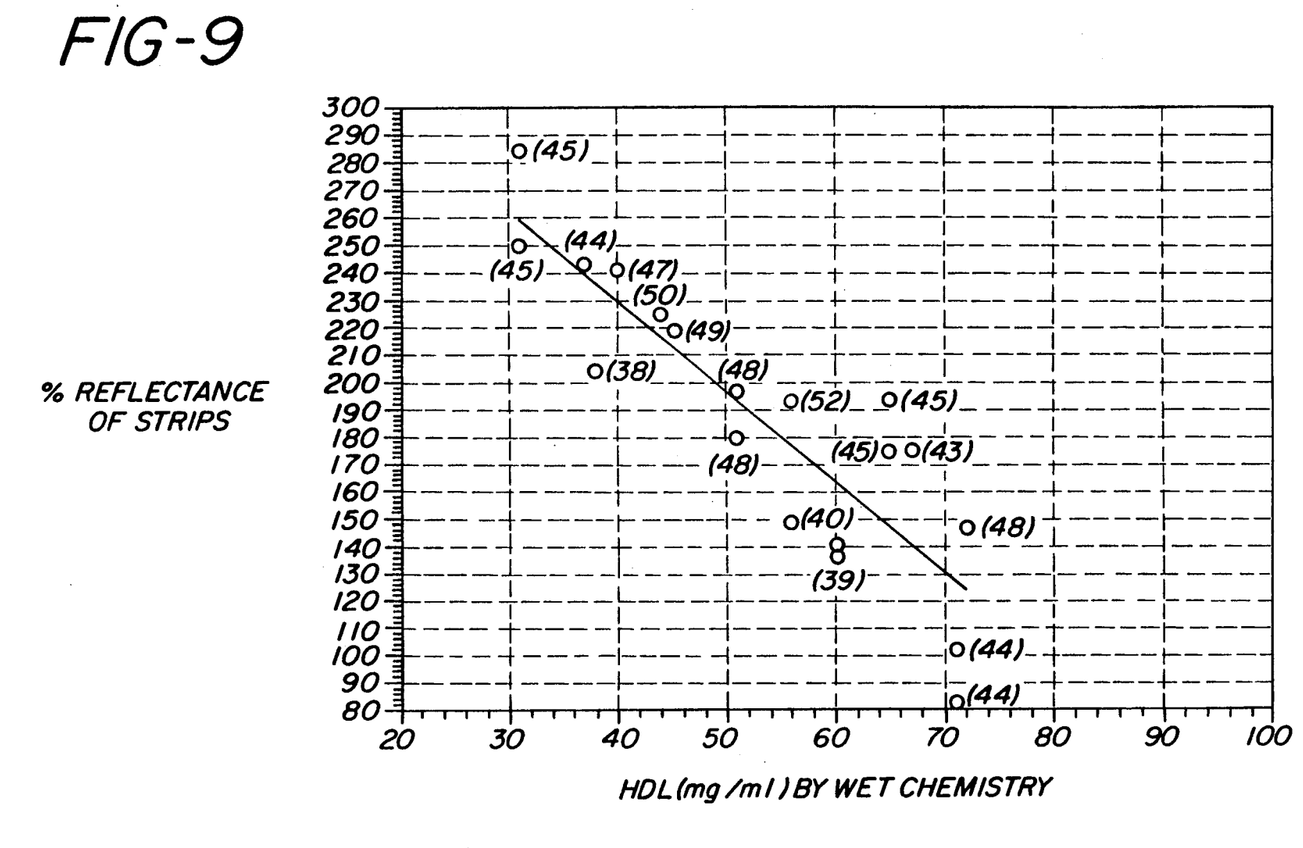

Devices with configuration as in FIG. 2 were used where the precipitant system was in carrier precipitant membrane 13. The concentrations of precipitants DS and $MgCl_2.6H_2O$ were 70 and 1421 mg/100 ml respectively The filtering membrane 5 in this case was a 0.8 micron polysulfone membrane. The procedure was similar to previous procedures and 40 microliter whole blood samples were applied. The response characteristics are plotted for one sample population in FIG. 9. The values in brackets show hematocrit values. The correlation coefficient by linear regression analysis for the entire population (higher and lower hematocrits) was quite good (0.87)

EXAMPLE 5

Figure 10:
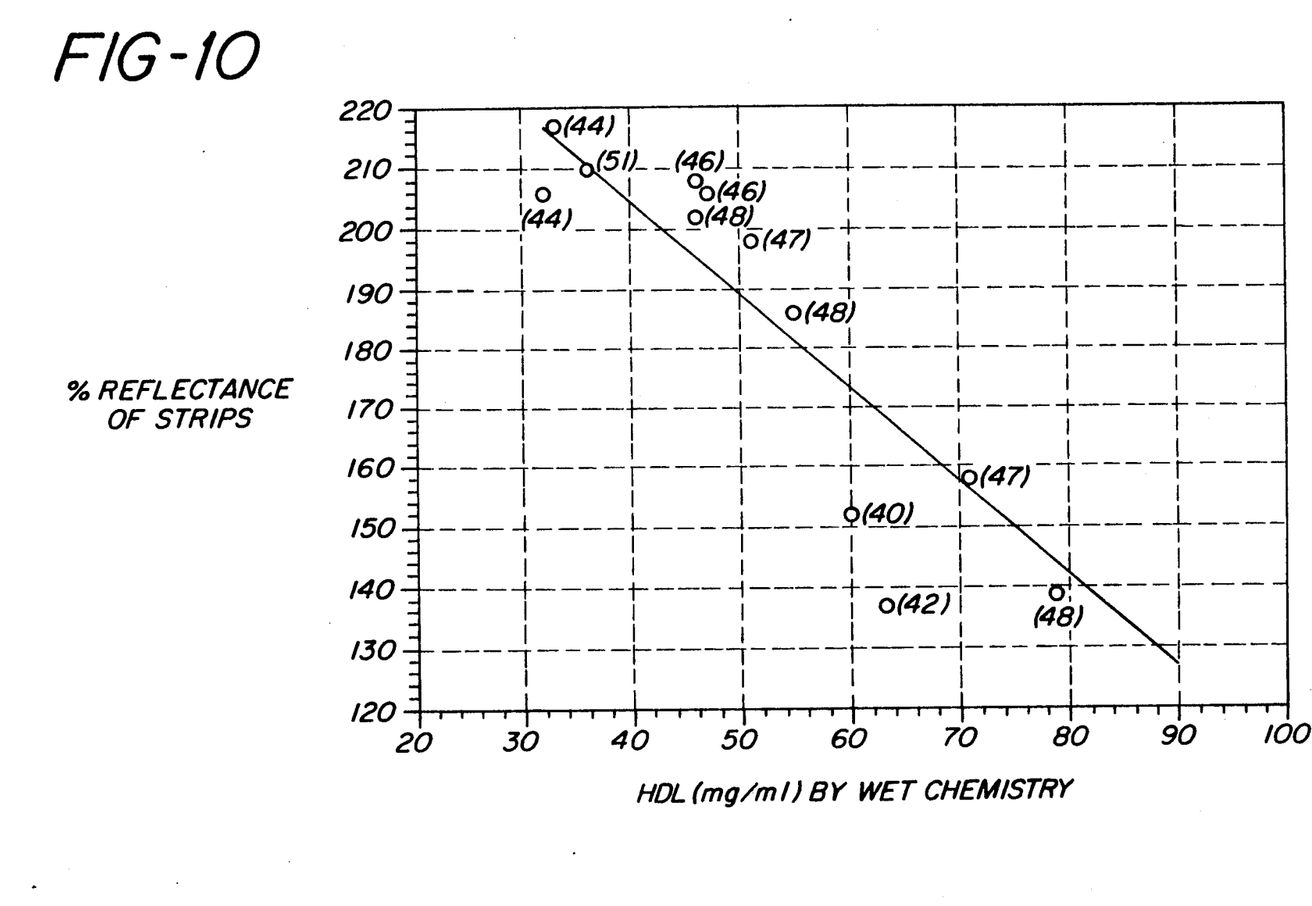

Example 4 was repeated with a new sample population. Again the correlation coefficient for the entire sample population was quite good (0.90) as seen in FIG. 10.

EXAMPLE 6

Devices similar to the configuration of FIG. 2 were used. The concentrations of the precipitants DS and $MgCl_2.6H_2O$ were 150 mg and 3045 mg/100 ml respectively. The filtering membrane in this case was a very thin (approximately 25 micron thickness) polycarbonate with 0.4 micron cylindrical pores (Poretics Corp.). 35 microliter blood samples were used and a sample population of 16 patients was used whose hematocrit values ranged from 38–51%.

Figure 11:
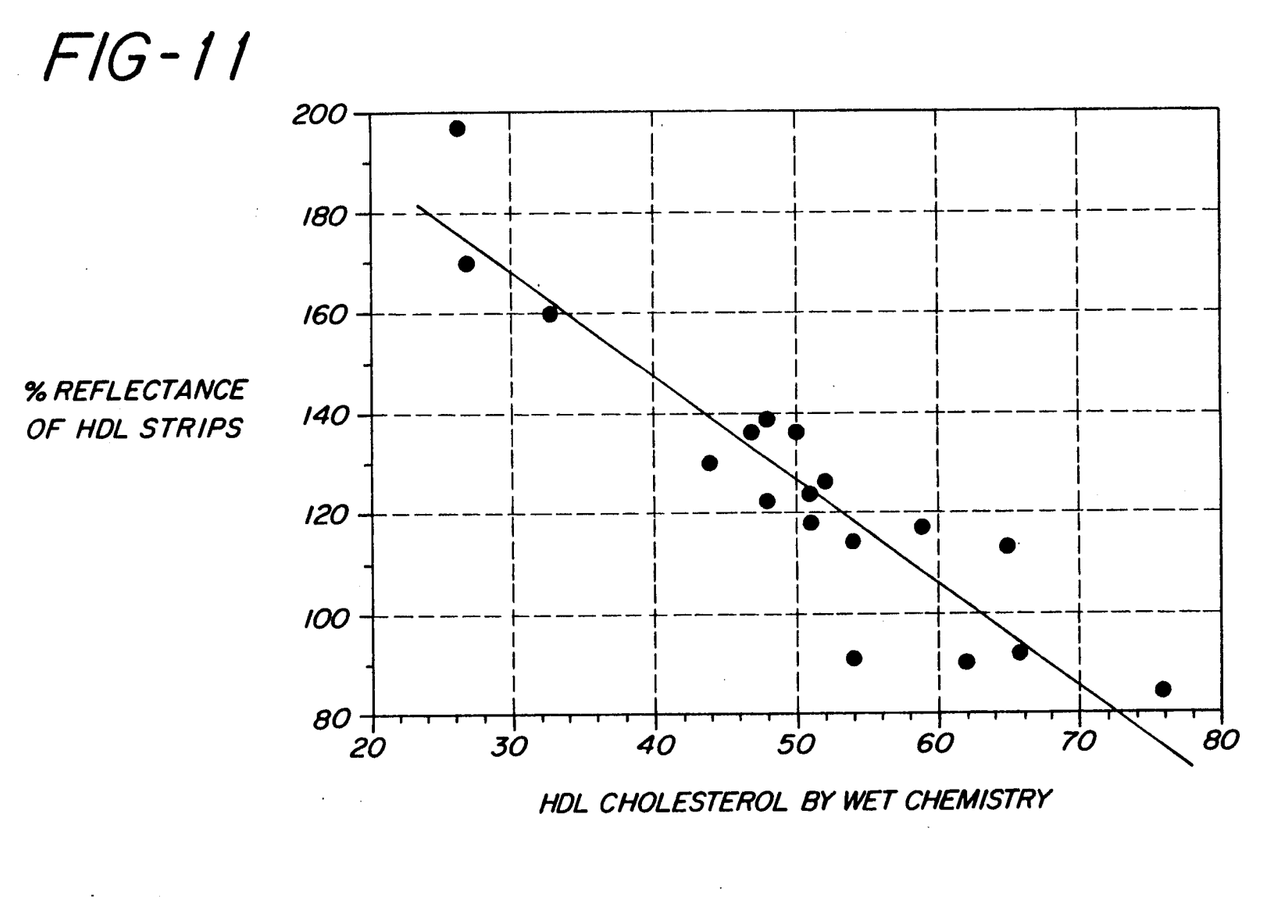

The strips gave good uniform colors with reaction completion times usually under 90 seconds and the correlation coefficient for the entire population was quite good (0.92) as seen in FIG. 11.

Obviously, numerous modifications and variations of the present invention are possible in light of the above teachings. It is therefore understood that within the scope of the appended claims, the invention may be practiced otherwise than as specifically described herein.

What is claimed is:

1. A device for determining HDL cholesterol by obtaining plasma from whole blood and determining HDL level from the plasma which comprises:
   (a) a physical transport medium;
   (b) a microporous plasma separation membrane having a first surface against said physical transport medium and having a second surface opposite and away from said physical transport medium;
   (c) a filtering membrane having a first surface and a second surface and being capable of filtering LDL and VLDL precipitates from a blood or plasma flow containing these, said filtering membrane having its first surface in contact with said microporous plasma separation membrane;

(d) at least one plasma collecting test membrane in contact with a portion of said second surface of said filtering membrane and having one or more reactants therein capable of reacting with said plasma to display at least one characteristic of HDL cholesterol; and, (e) LDL and VLDL reactants to form LDL and VLDL precipitates, said reactants being located in one or more of said microporous plasma separation membrane, said filtering membrane and said physical transport medium.

2. The device of claim 1 wherein a portion of said physical transport medium is not in contact with the microporous plasma separation membrane and is exposed for applying a sample of blood thereto.

3. The device of claim 1 wherein said physical transport medium relies, at least in part, on capillary forces to move the blood.

4. The device of claim 3 wherein said physical transport medium is a transport membrane sheet.

5. The device of claim 3 wherein said physical transport medium is an open structured mesh with openings of at least 1 micron in size and having hydrophilic surfaces.

6. The device of claim 3 wherein said microporous plasma separation membrane has a nominal pore size of about 0.02 to about 10 microns.

7. The device of claim 1 wherein said physical transport medium is a transport membrane sheet.

8. The device of claim 7 wherein said transport membrane sheet is a sheet of fabric selected from woven fabric, non-woven fabric, gauze and monofilament yarn.

9. The device of claim 1 wherein said LDL and VLDL reactants are contained in said physical transport medium.

10. The device of claim 1 wherein said physical transport medium constitutes grooves or channels formed on an inert substrate to promote movement of blood.

11. The device of claim 10 wherein said LDL and VLDL reactants are contained within the grooves or channels formed in said inert substrate.

12. The device of claim 1 wherein said physical transport medium is an open-structured mesh with openings of at least 1 micron in size and having hydrophilic surfaces.

13. The device of claim 1 wherein said LDL and VLDL reactants are contained in said microporous plasma separation membrane.

14. The device of claim 1 wherein said microporous plasma separation membrane has a nominal pore size of about 0.02 to about 10 microns.

15. The device of claim 1 wherein said microporous plasma separation membrane is a skinned membrane.

16. The device of claim 21 wherein said microporous plasma separation membrane is cellulosic.

17. The device of claim 1 wherein said microporous plasma separation membrane is of nitrocellulose.

18. The device of claim 1 wherein said filtering membrane is a membrane having a pore size of less than about 1 micron.

19. The device of claim 18 wherein said filtering membrane has a pore size of about 0.2 to about 0.8 microns.

20. The device of claim 18 wherein said filtering membrane is an asymmetric membrane with the second surface in contact with the plasma collecting test membrane having smaller pores in the pore size range of 0.01 to 0.1 micron.

21. The device of claim 18 wherein said filtering membrane has uniform cylindrical pores.

22. The device of claim 1 further comprising:

(f) an absorbent storage medium connected to said physical transport medium wherein said physical transport medium moves excess blood to said absorbent storage medium to prevent excess blood from retarding the effectiveness of said plasma collecting test membrane.

23. The device of claim 22 further including at least one inert substrate to which at least one of said microporous plasma separation membrane, said plasma collecting test membrane and said physical transport medium is connected.

24. The device of claim 1 wherein said plasma collecting test membrane includes one or more reactants which react with HDL cholesterol in said plasma to effect colorimetric reactions of HDL cholesterol for colorimertic determination of HDL cholesterol level.

25. The device of claim 1 further including at least one inert substrate to which at least one of said microporous plasma separation membrane, said plasma collecting test membrane and said physical transport medium is connected.

26. The device of claim 25 wherein said inert substrate support contains grooves or channels to promote movement of blood.

27. The device of claim 26 wherein said LDL and VLDL reactants are located in said grooves or channels in inert substrate support.

28. The device of claim 1 which further comprises:

(g) a top sheet containing at least one orifice through which a blood sample may be applied onto the physical transport medium, and at least a portion of this top sheet overlying said plasma collecting test membranes, said portion having transparent areas to view one or more colorimetric reactions.

29. The device of claim 28 wherein portions of said transparent areas on the top sheet havwe apertures to ensure oxygen transport to the plasma collecting test membrane for reactions that utilize oxygen.

30. The device of claim 29 wherein said apertures for oxygen transport are covered by transparent oxygen permeable membranes.

31. A device for determining HDL cholesterol by obtaining plasma from whole blood and determining HDL level from the plasma which comprises:

(a) a physical transport medium;

(b) a filtering membrane having a first surface and a second surface and being capable of filtering LDL and VLDL precipitates from a blood or plasma flow containing these, said filtering membrane having its first surface in contact with physical transport medium;

(c) a microporous plasma separation membrane having a first surface against the second surface of filtering membrane and having a second surface opposite and away from said second surface of said filtering membrane;

(d) at least one plasma collecting test membrane in contact with a portion of said second surface of said microporous plasma separation membrane and having one or more reactants therein capable of reacting with said plasma to display at least one characteristic of HDL cholesterol; and, (e) LDL and VLDL reactants to form LDL and VLDL precipitants, said reactants being located in one or more of said filtering membrane and said physical transport medium.

32. The device of claim 31 wherein a portion of said physical transport medium is not in contact with said filtering membrane and is exposed for applying a sample of blood thereto.

33. The device of claim 31 wherein said physical transport medium relies, at least in part, on capillary forces to move the blood.

34. The device of claim 33 wherein said physical transport medium is a transport membrane sheet.

35. The device of claim 33 wherein said physical transport medium is an open structured mesh with openings of at least 1 micron in size and having hydrophilic surfaces.

36. The device of claim 33 wherein said microporous plasma separation membrane has a nominal pore size of about 0.02 to about 10 microns.

37. The device of claim 31 wherein said physical transport medium is a transport membrane sheet.

38. The device of claim 37 wherein said transport membrane sheet is a sheet of fabric selected from woven fabric, non-woven fabric, gauze and monofilament yarn.

39. The device of claim 31 wherein said LDL and VLDL reactants are contained in said physical transport medium.

40. The device of claim 31 wherein said physical transport medium constitutes grooves or channels formed on an inert substrate to promote movement of blood.

41. The device of claim 40 wherein said LDL and VLDL reactants are contained in said grooves or channels formed on said inert substrate.

42. The device of claim 31 wherein said physical transport medium is an open-structured mesh with openings of at least 1 micron in size and having hydrophilic surfaces.

43. The device of claim 31 wherein said microporous plasma separation membrane has a nominal pore size of about 0.02 to about 10 microns.

44. The device of claim 31 wherein said mocroporous plasma separation membrane is a skinned membrane.

45. The device of claim 31 wherein said microporous plasma separation membrane is cellulosic.

46. The device of claim 31 wherein said microporous plasma separation membrane is of nitrocellulose.

47. The device of claim 31 wherein said filtering membrane is a membrane having a pore size of less than about 1 micron.

48. The device of claim 47 wherein said filtering membrane has a pore size of about 0.01 to about 0.8 microns.

49. The device of claim 47 wherein said filtering membrane is an asymmetric membrane with the second surface in contact with the microporous plasma separating membrane having smaller pores in the pore size range of 0.01 to 0.1 micron.

50. The device of claim 47 wherein said filtering membrane has uniform cylindrical pores.

51. The device of claim 31 further comprising:
(f) an absorbent storage medium connected to said physical transport medium wherein said physical transport medium moves excess blood to said absorbent storage medium to prevent excess blood from retarding the effectiveness of said plasma collecting test membrane.

52. The device of claim 51 further including at least one inert substrate to which at least one of said microporous plasma separation membrane, said plasma collecting test membrane and said physical transport medium is connected.

53. The device of claim 31 wherein said plasma collecting test membrane includes one or more reactants which react with HDL cholesterol in said plasma to effect colorimetric reactions of HDL for colorimetric determination of HDL cholesterol level.

54. The device of claim 31 further including at least one inert substrate to which at least one of said microporous separation membrane, said plasma collecting test membrane and said physical transport medium is connected.

55. The device of claim 54 wherein said inert substrate support contains grooves or channels to promote movement of blood.

56. The device of claim 55 wherein said LDL and VLDL reactants are located in said grooves or channels in said inert substrate support.

57. The device of claim 31 which further comprises:
(g) a top sheet containing at least one orifice through which a blood sample may be applied onto the physical transport medium, and at least a portion of this top sheet overlying said plasma collecting test membranes, said portion having transparent areas to view one or more colorimetric reactions.

58. The device of claim 57 wherein portions of said transparent areas on the top sheet have apertures to ensure oxygen transport to the plasma collecting test membrane for reactions that utilize oxygen.

59. The device of claim 58 wherein said apertures for oxygen transport are covered by transparent oxygen permeable membranes.

60. A device for determining HDL cholesterol by obtaining plasma from whole blood and determining HDL level from the plasma which comprises:
(a) a physical transport medium;
(b) a microporous plasma separation membrane having a first surface against said physical transport medium and having a second surface opposite and away from said physical transport medium.
(c) A carrier precipitant membrane containing reactants for precipitation of LDL and VLDL from plasma having a first surface and a second surface, said first surface in contact with said microporous plasma separation membrane and said second surface opposite and away from said microporous plasma separation membrane;
(d) a filtering membrane having a first surface and a second surface and being capable of filtering LDL and VLDL precipitates from a blood or plasma flow containing these, said filtering membrane having its first surface in contact with said carrier precipitant membrane; and,
(e) at least one plasma collecting test membrane in contact with a portion of said second surface of said microporous plasma separation membrane and having one or more reactants therein capable of reacting with said plasma to display at least one characteristic of HDL cholesterol.

61. The device of claim 60 wherein a portion of said physical transport medium is not connected to the microporous plasma separation membrane and is exposed for applying a sample of blood thereto.

62. The device of claim 60 wherein said physical transport medium relies, at least in part on capillary forces to move the blood.

63. The device of claim 62 wherein said physical transport medium is a transport membrane sheet.

64. The device of claim 62 wherein said physical transport medium is an open structured mesh with openings of at least 1 micron in size and having hydrophilic surfaces.

65. The device of claim 62 wherein said microporous plasma separation membrane has a nominal pore size of about 0.02 to about 10 microns.

66. The device of claim 60 wherein said physical transport medium is a transport membrane sheet.

67. The device of claim 66 wherein said transport membrane sheet is a sheet of fabric selected from woven fabric, non-woven fabric, gauze and monofilament yarn.

68. The device of claim 60 wherein said physical transport medium constitutes grooves or channels formed on an inert substrate to promote movement of blood.

69. The device of claim 60 wherein said physical transport medium is an open-structured mesh with openings of at least 1 micron in size and having hydrophilic surfaces.

70. The device of claim 60 wherein said microporous plasma separation membrane has a nominal pore size of about 0.02 to about 10 microns.

71. The device of claim 60 wherein said micorporous plasma separation membrane is a skinned membrane.

72. The device of claim 60 wherein said microporous plasma separation membrane is cellulosic.

73. The device of claim 60 wherein said microporous plasma separation membrane is of nitrocellulose.

74. The device of claim 60 wherein said filtering membrane is a membrane having a pore size of less than about 1 micron.

75. The device of claim 74 wherein said filtering membrane has a pore size of about 0.01 to about 0.8 microns.

76. The device of claim 74 wherein said filtering membrane has uniform cylindrical pores.

77. The device of claim 60 wherein said carrier precipitant membrane has pore sizes in the range of 0.01 to 25 microns.

78. The device of claim 60 wherein said carrier precipitant membrane is polysulfone.

79. The device of claim 60 further comprising:
(f) an absorbent storage medium connected to said physical transport medium wherein said physical transport medium moves excess blood to said absorbent storage medium to prevent excess blood from retarding the effectiveness of said plasma collecting test membrane.

80. The device of claim 79 further including at least one inert substrate to which at least one of said microporous plasma separation membrane, said carrier precipitant membrane, said plasma collecting test membrane and said physical transport medium is connected.

81. The device of claim 60 wherein said plasma collecting test membrane includes one or more reactants which react with HDL cholesterol in said plasma to effect colorimetric reactions of HDL for colorimetric determination of HDL cholesterol level.

82. The device of claim 60 wherein said filtering membrane and said plasma collecting test membrane are combined into a single membrane.

83. The device of claim 82 wherein said single membrane is an asymmetric membrane with pore sizes in the range of 0.02 to 0.1 microns with the finer pores located in contact with said second surface of said carrier precipitant membrane.

84. The device of claim 83 wherein said asymmetric membrane includes one or more reactants which react with HDL cholesterol in said plasma to effect colorimetric reactions of HDL for colorimetric determination of HDL cholesterol level.

85. The device of claim 60 wherein said carrier precipitant membrane and said filtering membrane are combined into a single membrane.

86. The device of claim 85 wherein said single membrane is an asymmetric membrane with the finer pores in the pore range of 0.02 to 1.0 micron located in contact with said first surface of said plasma collecting test membrane.

87. The device of claim 85 wherein said single membrane is a membrane with ultramicroporous structure with pore size in the range of 0.01 to 0.1 microns.

88. The device of claim 60 further including at least one inert substrate to which at least one of said microporous separation membrane, said carrier precipitant membrane, said plasma collecting test membrane and said physical transport medium is connected.

89. The device of claim 60 which further comprises:
(g) a top sheet containing at least one orifice through which a blood sample may be applied onto the physical transport medium, and at least a portion of this top sheet overlying said plasma collecting test membrane, said portion having transparent areas to view one or more colorimetric reactions.

90. The device of claim 89 wherein portions of said transparent areas on the top sheet have apertures to ensure oxygen transport to the plasma collecting test membrane for reactions that utilize oxygen.

91. The device of claim 90 wherein said apertures for oxygen transport are covered by transparent oxygen permeable membranes.

* * * * *

UNITED STATES PATENT AND TRADEMARK OFFICE
CERTIFICATE OF CORRECTION

PATENT NO. : 5,135,716
DATED : August 4, 1992
INVENTOR(S) : Yatin B. Thakore

It is certified that error appears in the above-identified patent and that said Letters Patent is hereby corrected as shown below:

In column 14, line 61, change "microporous plasma separation" to --filtering--.

Signed and Sealed this

Twenty-second Day of May, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO. : 5,135,716
DATED : August 4, 1992
INVENTOR(S) : Yatin B. Thakore

It is certified that error appears in the above-identified patent and that said Letters Patent is hereby corrected as shown below:

Column 14,
Line 61, change "microporous plasma separation" to --filtering--.

Signed and Sealed this

Third Day of July, 2001

*Attest:*

NICHOLAS P. GODICI
*Attesting Officer*     *Acting Director of the United States Patent and Trademark Office*